US012605501B2

(12) United States Patent
Pic et al.

(10) Patent No.: US 12,605,501 B2
(45) Date of Patent: Apr. 21, 2026

(54) AGENT DELIVERY DEVICES AND METHODS OF USING THE SAME

(71) Applicant: Boston Scientific Scimed, Inc., Maple Grove, MN (US)

(72) Inventors: Andrew Pic, Northboro, MA (US); Daniel Congdon, Somerville, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1018 days.

(21) Appl. No.: 17/662,498

(22) Filed: May 9, 2022

(65) Prior Publication Data

US 2022/0355024 A1      Nov. 10, 2022

Related U.S. Application Data

(60) Provisional application No. 63/186,551, filed on May 10, 2021.

(51) Int. Cl.
    A61M 5/14          (2006.01)
    A61M 5/145         (2006.01)
(52) U.S. Cl.
    CPC ...... A61M 5/1408 (2013.01); A61M 5/14526 (2013.01); *A61M 2005/14506* (2013.01)
(58) Field of Classification Search
    CPC ............ A61M 5/1408; A61M 5/14526; A61M 2005/14506; A61M 11/02; A61M 15/0005; A61B 2017/00548; A61B 17/00491; A61B 2017/00495; A61B 2017/00522
    See application file for complete search history.

(56) References Cited

U.S. PATENT DOCUMENTS

| | | | |
|---|---|---|---|
| 4,785,996 A | 11/1988 | Ziecker et al. | |
| 2003/0181917 A1* | 9/2003 | Gertner | A61M 15/0066 |
| | | | 604/24 |
| 2003/0187408 A1* | 10/2003 | Marx | A61B 17/00491 |
| | | | 424/94.64 |

(Continued)

FOREIGN PATENT DOCUMENTS

| | | |
|---|---|---|
| WO | 9820931 A1 | 5/1998 |
| WO | 9917833 A1 | 4/1999 |

OTHER PUBLICATIONS

International Search Report and Written Opinion issued in International Application No. PCT/US2022/072199, mailed Aug. 16, 2022 (14 pages).

*Primary Examiner* — James D Ponton
(74) *Attorney, Agent, or Firm* — Bookoff McAndrews, PLLC

(57)                ABSTRACT

A medical device that includes a body configured to store a first substance and a second substance, a shaft extending distally from the body and having a distal end, and a pressure source in fluid communication with the first substance, the second substance, and the shaft. Pressurized medium from the pressure source is configured to deliver the first substance through the shaft and out of the distal end, deliver the second substance through the shaft, separate from the first substance, and out of the distal end, and be delivered through the shaft separate from the first substance and the second substance, and out of the distal end. The pressurized medium mixes the first substance and the second substance externally of the shaft as the first and second substances exit the distal end.

20 Claims, 3 Drawing Sheets

(56) References Cited

U.S. PATENT DOCUMENTS

| | | | |
|---|---|---|---|
| 2004/0059283 A1* | 3/2004 | Kirwan | B05B 7/2437 |
| | | | 604/82 |
| 2016/0074617 A1 | 3/2016 | Gharazozloo et al. | |
| 2019/0343980 A1 | 11/2019 | Gittard et al. | |
| 2020/0100986 A1 | 4/2020 | Pic et al. | |

* cited by examiner

AGENT DELIVERY DEVICES AND METHODS OF USING THE SAME

CROSS-REFERENCE TO RELATED APPLICATIONS

This application claims the benefit of priority from U.S. Provisional Application No. 63/186,551, filed on May 10, 2021, which is incorporated by reference herein in its entirety.

TECHNICAL FIELD

Various aspects of this disclosure relate generally to medical delivery systems, devices, and related methods. For example, the disclosure includes systems, devices, and related methods for delivering a fluid mixture to a target treatment site of a subject.

BACKGROUND

Tissue undergoing a surgical procedure (e.g., dissection, resection, etc.) may be prone to experiencing various injury, such as, perforations, wounds, contusions, and more. Such injuries may cause various health issues for a patient, including delayed leaks, infection, lesions, or other post procedure complications. Medical devices capable of preventing, treating, or protecting tissue are limited, and particularly endoscopic devices for delivering a protective covering onto areas of the tissue that may be injury prone within the gastrointestinal tract of a patient. Devices and methods for separately delivering multiple substances that form a protective covering at a target treatment site during application of the substances may be further limited.

SUMMARY

Aspects of the disclosure relate to, among other things, systems, devices, and methods for treating a target treatment site using a delivery device providing multiple substances for creating a protective covering at the target treatment site. For example, the device may include a first substance and a second substance that are separated in isolation from one another during delivery to the target treatment site. They may be applied simultaneously to the target treatment site to form a solution mixture within the subject (e.g., patient) consisting of the protective covering. Aspects of this disclosure may extend to a device including more than two substances and/or parts of agent for mixture and application to a target treatment site. Each of the aspects disclosed herein may include one or more of the features described in connection with any of the other disclosed aspects.

According to an example, a medical device includes a body configured to store a first substance and a second substance; a shaft extending distally from the body and having a distal end; and a pressure source in fluid communication with the first substance, the second substance, and the shaft, wherein pressurized medium from the pressure source is configured to: (i) deliver the first substance through the shaft and out of the distal end; (ii) deliver the second substance through the shaft, separate from the first substance, and out of the distal end; and (iii) be delivered through the shaft separate from the first substance and the second substance, and out of the distal end, such that the pressurized medium mixes the first substance and the second substance externally of the shaft as the first and second substances exit the distal end.

Any of the medical devices described herein may include any of the following features. The first substance and the second substance exit the distal end of the shaft in the form of a plurality of droplets. The pressurized medium is configured to exit the distal end of the shaft at a predefined velocity to disassemble a polymer chain of the plurality of droplets of each of the first substance and the second substance. The pressurized medium is configured to atomize the plurality of droplets of the first substance and the second substance at a position distal to the distal end of the shaft. The pressurized medium is configured to generate a stream sprayed from the distal end of the shaft. The pressurized medium is configured to generate a mist sprayed from the distal end of the shaft. The shaft includes a first channel for receiving the first substance, a second channel for receiving the second substance, and third channel for receiving the pressurized medium. The body includes a first container for storing the first substance and a second container for storing the second substance, such that the first substance and the second substance are isolated from one another within the body. The first container is in fluid communication with the pressure source and the first channel of the shaft, and the second container is in fluid communication with the pressure source and the second channel of the shaft. The first container includes a first intake tube extending into a cavity of the first container, the first intake tube having an opening that is positioned below a surface level of the first substance within the cavity. The pressurized medium is configured to enter the first container and generate pressure within the cavity to transfer the first substance through the opening and up the first intake tube. The pressure source is configured to simultaneously deliver the pressurized medium to the first container, the second container, and the third lumen of the shaft. The pressure source is disposed within the body and includes a gas canister, wherein the pressurized medium includes compressed gas stored in the canister in a supercritical or liquid form at about 850 psi. The first substance and the second substance each has a viscosity greater than 1 centipoise.

According to another example, a medical device includes a body; a first container disposed within the body and configured to contain a first substance; a second container disposed within the body and configured to contain a second substance; and a pressure source disposed within the body and storing a pressurized medium, the pressure source being in fluid communication with the first container and the second container; wherein first and second portions of the pressurized medium are delivered into the first container and the second container respectively to eject at least a portion of the first substance and at least a portion of the second substance out of the device at first and second velocities, respectively; and wherein a third portion of the pressurized medium is ejected out of the device at a third velocity that is greater than the first velocity and the second velocity, to mix the first substance and the second substance together outside of the device.

Any of the medical devices described herein may include any of the following features. At least the portion of the first substance and at least a portion of the second substance form a plurality of droplets when ejected out of the device; and the pressurized medium atomizes the plurality of droplets of the first substance and the plurality of droplets of the second substance at a position outside of the device. The pressurized medium sprays a stream or a mist of the first substance and the second substance from the device. The first container includes a first intake tube extending into a cavity of the first container, the first intake tube including an opening submerged within the first substance within the cavity. The pressurized medium enters the first container and increases a pressure within the cavity to transfer the first substance up the first intake tube via the opening.

According to a further example, a method of treating a subject includes positioning a medical device at a target tissue of the subject, wherein the medical device comprises: a first container storing a first substance; a second container storing a second substance; and a pressure source storing a pressurized medium, the pressure source in fluid communication with the first container and the second container; transferring first and second portions of the pressurized medium from the pressure source to the first container and the second container respectively to deliver at least a portion of the first substance and at least a portion of the second substance out of the medical device; transferring a third portion of the pressurized medium from the pressure source to an exterior of the medical device to mix the first substance and the second substance external from the medical device.

It may be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate exemplary aspects of the disclosure and together with the description, serve to explain the principles of the disclosure.

DETAILED DESCRIPTION

Figure 1:
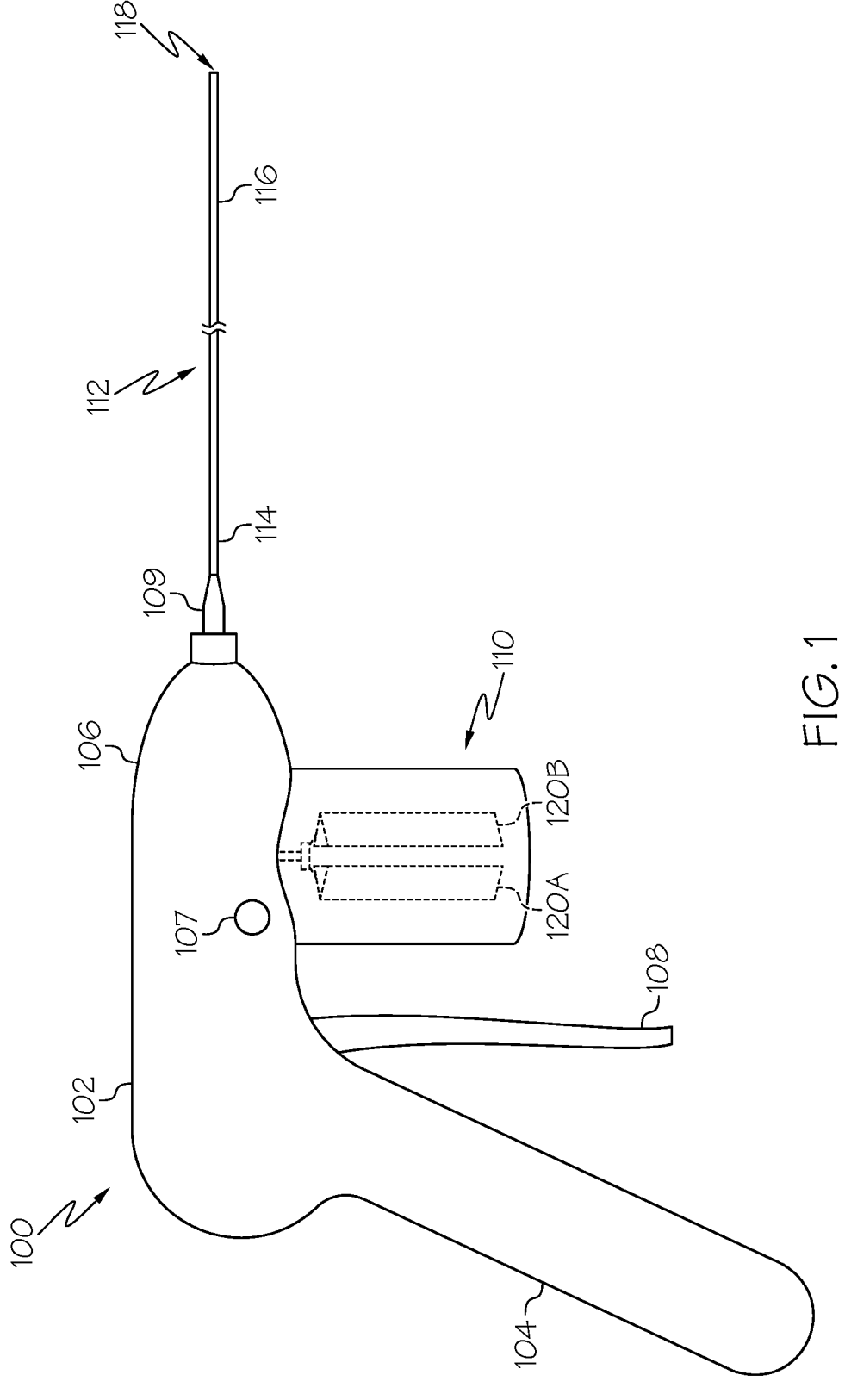
FIG. 1 is a side view of an exemplary medical device including a first fluid container and a second fluid container, according to aspects of this disclosure.

Medical delivery devices with features for facilitating a mixture and application of multiple substances (e.g., two or more) to a target treatment site are included herein. A target treatment site for receiving the protective covering may include a tissue wall, such as an esophagus or other part of the gastrointestinal system of the patient. The devices herein may include features for delivering multiple substances to the target treatment site and mixing the substances at the target treatment site, and external of the device, during application to form the protective covering.

Examples of the disclosure include systems, devices, and methods for delivering substances to a target treatment site within a subject (e.g., patient). In examples, accessing a patient's esophagus includes endoluminal placement of the medical device into the target treatment site. Placement of the medical device may be via a catheter, scope (endoscope, bronchoscope, colonoscope, gastroscope, etc.), tube, or sheath, inserted into an anatomical passageway via a natural orifice or via laparoscopy. The orifice can be, for example, the nose, mouth, or anus, and the placement can be in any portion of the GI tract, including the esophagus, stomach, duodenum, large intestine, or small intestine. Placement also can be in other organs or other bodily spaces reachable via the GI tract, other body lumens, or openings in the body, including via laparoscopy. This disclosure is not limited to any particular medical procedure or treatment site within a body.

Reference will now be made in detail to aspects of the disclosure, examples of which are illustrated in the accompanying drawings. Wherever possible, the same or similar reference numbers will be used through the drawings to refer to the same or like parts. The term "distal" refers to a portion farthest away from a user when introducing a device into a patient. By contrast, the term "proximal" refers to a portion closest to the user when placing the device into the subject. As used herein, the terms "comprises," "comprising," or any other variation thereof, are intended to cover a non-exclusive inclusion, such that a process, method, article, or apparatus that comprises a list of elements does not necessarily include only those elements, but may include other elements not expressly listed or inherent to such process, method, article, or apparatus. The term "exemplary" is used in the sense of "example," rather than "ideal." As used herein, the terms "about," "substantially," and "approximately," indicate a range of values within +/−5% of a stated value.

Examples of the disclosure may relate to devices and methods for performing various medical procedures and/or treating portions of the large intestine (colon), small intestine, cecum, esophagus, any other portion of the gastrointestinal tract, and/or any other suitable patient anatomy (collectively referred to herein as a "target treatment site"). As mentioned above, this disclosure is not limited to any specific medical device or method, and aspects of the disclosure may be used in connection with any suitable medical tool and/or medical method, at any suitable site within the body. Various examples described herein include single-use or disposable medical devices.

FIG. 1 shows an exemplary medical device 100 in accordance with one or more examples of this disclosure. Medical device 100 may include a body 102 defined by a proximal portion 104 and a distal portion 106. In the example, body 102 may be sized and shaped in the form of a handheld device, such as, for example, a spray gun. In this instance, proximal portion 104 may define a handle of body 102 and distal portion 106 may define a barrel of body 102. Medical device 100 may include an actuator 108 movably coupled to body 102 adjacent to proximal portion 104. Actuator 108 may be operatively coupled to a pressurized medium source 130 disposed within body 102 (see FIG. 2), and configured to activate the pressurized medium source 130 in response to actuation (e.g., proximal movement) of actuator 108 relative to body 102.

Medical device 100 may further include a canister 110 coupled to body 102 adjacent to distal portion 106. In the example, canister 110 may be at least partially received in body 102 along a bottom surface of distal portion 106. In some embodiments, canister 110 may be releasably coupled to body 102, such that canister 110 may be selectively removed from body 102. In the example, medical device 100 may include a release mechanism 107 for decoupling canister 110 from body 102. Release mechanism 107 may include various suitable actuators, such as, for example, a depressible button. In another example, canister 110 may be decoupled from body 102 by applying a downward pulling force onto canister 110 to separate canister 110 from body 102. In this instance, release mechanism 107 may be omitted entirely. In other embodiments, canister 110 may be securely fixed to distal portion 106 such that canister 110 is not removable from body 102.

As shown and described further herein, canister 110 may define an enclosure for housing a plurality of fluid containers, including but not limited to, at least a first fluid container 120A and a second fluid container 120B. In other embodiments, canister 110 may include one or more partitions in lieu of the plurality of fluid containers. In this instance, the one or more partitions may define a plurality of fluid chambers (e.g., at least two) within canister 110 for storing a plurality of fluid substances. In some embodiments, canister 110 may include an opaque exterior such that the first fluid container 120A and the second fluid container 120B are not viewable from an exterior of medical device 100. In other embodiments, canister 110 may include a transparent exterior such that the pair of fluid containers 120A, 120B, and more particularly the volume of contents in each fluid container 120A, 120B, are visible from an exterior of medical device 100.

Still referring to FIG. 1, medical device 100 may further include a nozzle 109 extending distally from distal portion 106, and a shaft 112 extending distally from nozzle 109. Nozzle 109 may be rotatably coupled to body 102 at distal portion 106, and fixed relative to shaft 112. Accordingly, rotation of nozzle 109 relative to body 102 may provide a corresponding rotation of shaft 112 relative to body 102. As described in further detail below, nozzle 109 may be configured to at least partially control a spray stream of medical device 100 from shaft 112.

Figure 4:
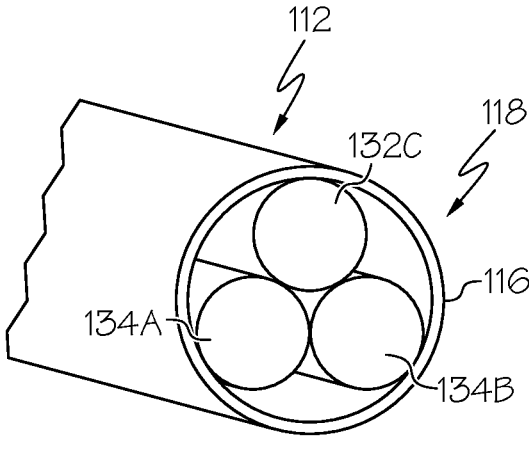
FIG. 4 is a partial perspective view of a distal end of the medical device of FIG. 1, according to aspects of this disclosure.

Shaft 112 may have a longitudinal length defined between a proximal end 114 and a distal end 116. Shaft 112 may have a flexible configuration such that proximal end 114 and distal end 116 may be configured to move (e.g., bend, twist, turn, deflect, etc.) relative to one another and body 102. Shaft 112 may define a lumen that is sized and shaped to receive a plurality of outlet lines (e.g., flexible tubes) from one or more components of medical device 100, such as, for example, pressurized medium source 130 and the pair of fluid containers 120A, 120B (see FIG. 2). Shaft 112 may further include an opening 118 at distal end 116, as best seen in FIG. 4.

Figure 2:
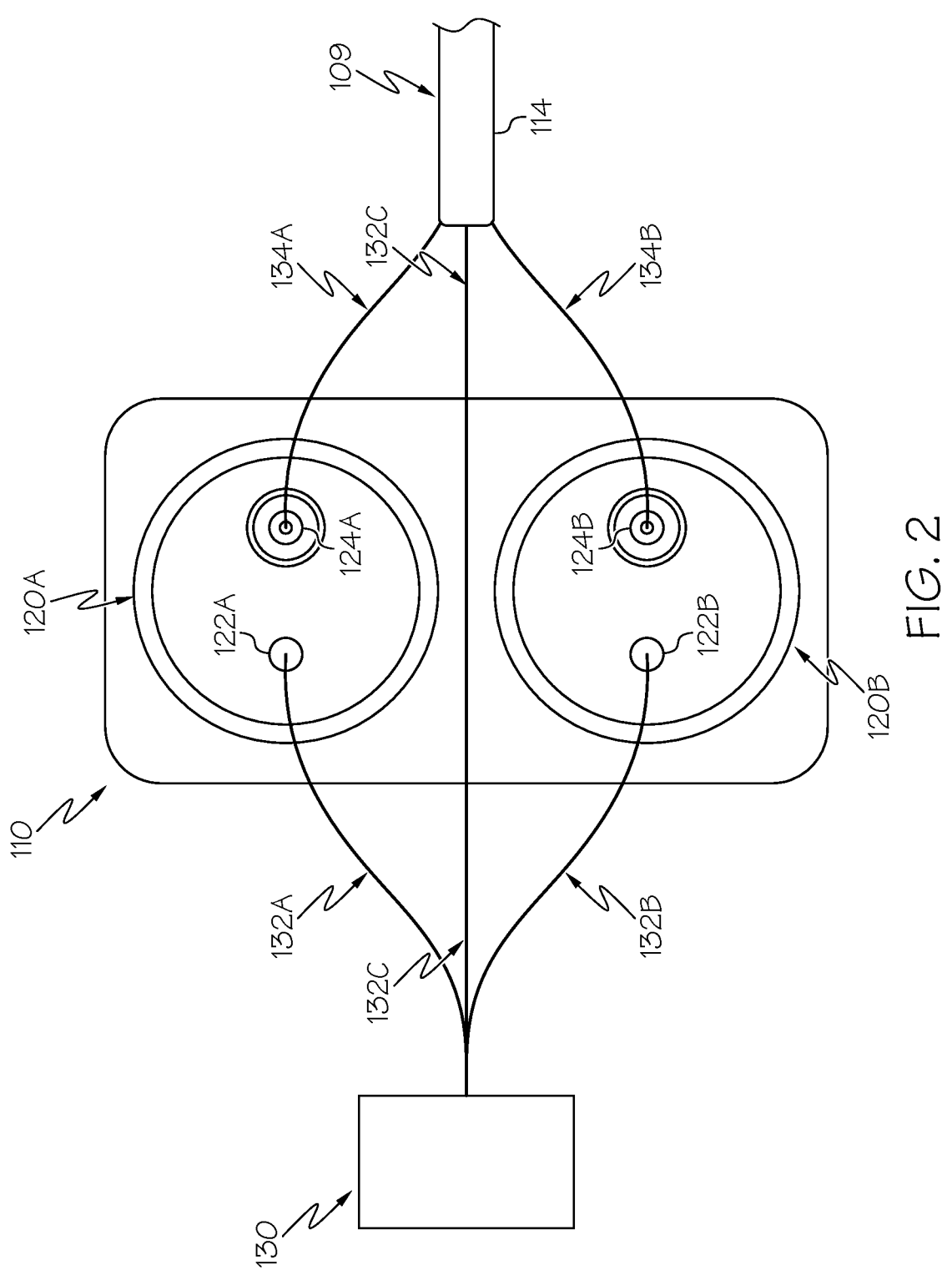
FIG. 2 is a schematic view of portions of the medical device of FIG. 1, with the first fluid container and the second fluid container coupled to a pressure source, according to aspects of this disclosure.

Referring now to FIG. 2, a schematic illustration of a fluidic system of medical device 100 is shown. Medical device 100 may include a pressurized medium source 130 (disposed within body 102), such as, for example, a pneumatic gas canister. Pressurized medium source 130 may be in fluid communication with each of the fluid containers 120A, 120B via a respective inlet line 132A, 132B (e.g., flexible tubes). In the example, medical device 100 may include at least a first fluid container 120A and a second fluid container 120B disposed within canister 110. In one example, fluid containers 120A, 120B may include coiled tubing capable of being flexibly deformed to various sizes, shapes, and/or configurations. First fluid container 120A may be fluidly coupled to pressurized medium source 130 via first inlet line 132A, and second fluid container 120B may be fluidly coupled to pressurized medium source 130 via second inlet line 132B. In further embodiments, pressurized medium source 130 may be positioned outside of body 102, and fluidly coupled to medical device 100 via a connector, such as, for example, a port.

Pressurized medium source 130 may be configured to store a pressurized medium. In an embodiment, the pressurized medium may include a compressed gas (e.g., carbon dioxide) stored in a supercritical or liquid form, such as at about 850 PSI. It should be understood that a capacity of pressurized medium source 130 may define an amount (weight) of pressurized medium that pressurized medium source 130 may store. Further, an available weight of pressurized medium stored in pressurized medium source 130 may correspond to a predetermined dose of fluid that medical device 100 may be capable of delivering during a procedure. By way of illustrative example, pressurized medium source 130 may store about 10 grams to 20 grams of carbon dioxide, such as, for example, 16 grams. In the example, medical device 100 may be configured such that storing 16 grams of pressurized medium may correspond to about 5 liters of pressurized medium output via the fluidic system of medical device 100 to deliver the predetermined dose.

Still referring to FIG. 2, each of the pair of fluid containers 120A, 120B may include an inlet port 122A, 122B that receives the respective inlet line 132A, 132B from pressurized medium source 130. In the example, first inlet line 132A and second inlet line 132B may have an inner diameter ranging from about 0.25 inches to 0.5 inches, such as 0.375 inches. Each of the pair of fluid containers 120A, 120B may further include an outlet port 124A, 124B that receives a respective outlet line 134A, 134B (e.g., flexible tubes). First outlet line 134A may fluidly couple first fluid container 120A with shaft 112, and second outlet line 134B may fluidly couple second fluid container 120B with shaft 112.

In the example, first outlet line 134A and second outlet line 134B may have an area ranging from about 0.0005 inches-squared to 0.0032 inches-squared, such as 0.0016 inches-squared. Each of first outlet line 134A and second outlet line 134B may extend through nozzle 109 and into a lumen of shaft 112. As shown and described further herein, each of the pair of outlet lines 134A, 134C may terminate at an opening 118 at distal end 116 of shaft 112 (see FIG. 4).

Medical device 100 may further include a fluid line 132C providing fluid communication between pressurized medium source 130 and shaft 112. Pressurized medium source 130 may be configured to deliver the pressurized medium directly to shaft 112 via fluid line 132C. Fluid line 132C may terminate at opening 118 of distal end 116, and adjacent to the pair of outlet lines 134A, 134B (see FIG. 4). Accordingly, it should be appreciated that the lumen of shaft 112 may be sized, shaped, and configured to receive a plurality of tubes and/or lines, such as, for example first outline line 134A, second outlet line 134B, and fluid line 132C. Shaft 112 may have a diameter ranging from about 0.02 inches to 0.08 inches, such as 0.04 inches. In other embodiments, shaft 112 may define a plurality of channels formed within the lumen, such that each of the lines 132C, 134A, 134B are fluidly coupled to at least one channel. In this instance, first outline line 134A, second outlet line 134B, and fluid line 132C are coupled to a respective channel of shaft 112 at proximal end 114, and thereby do not extend through shaft 112.

Figure 3:
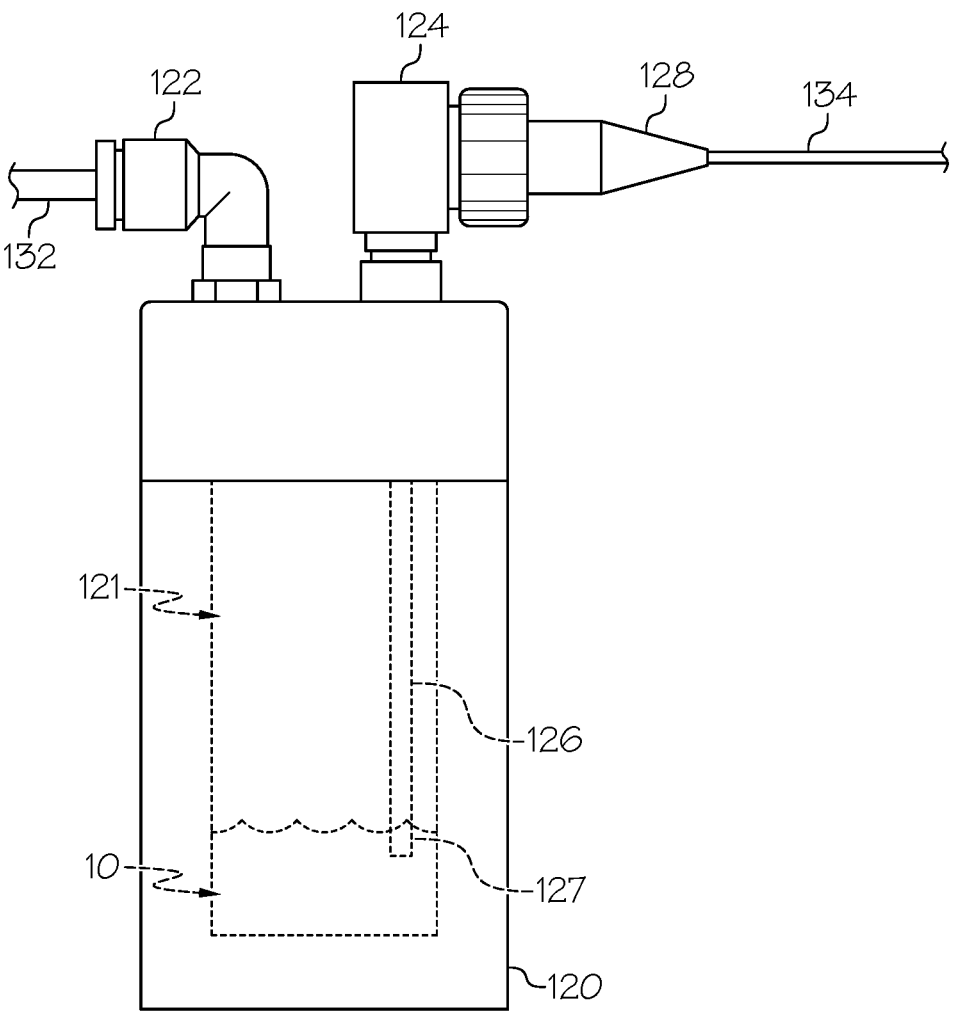
FIG. 3 is a partial side view of one of the fluid containers of the medical device of FIG. 1, according to aspects of this disclosure.

FIG. 3 depicts a fluid container 120 that may be representative of first fluid container 120A and second fluid container 120B described above. Fluid container 120 may include inlet port 122 and outlet port 124 along a top wall of fluid container 120. In other embodiments, one or more of inlet port 122 and/or outlet port 124 may be positioned along various other walls of fluid container 120, such as one or more of the sidewalls of fluid container 120. Fluid container 120 may further include an internal cavity 121 for storing at least one fluid substance 10. In an example, first fluid container 120A may store a first fluid substance, and second fluid container 120B may store a second fluid substance that is different than the first fluid substance. Each of the fluid substances 10 may generally have a high viscosity, such as, for example, a viscosity greater than about one centipoise, such as, for example, ranging between 30 centipoise to 11,000 centipoise. As described in further detail below, the first and second fluid substances may form a solution mixture when combined with one another for use in treating a target site (e.g., tissue). The solution mixture may include an adhesive capable of providing a protective barrier over a perforation or other injury prone area of tissue. In other embodiments, the resulting solution may include various other agents formed in response to the mixture of two or more substances.

Fluid container 120 may further include an intake tube 126 disposed within internal cavity 121. Intake tube 126 may be fluidly coupled to outlet port 124 and at least partially submerged in the fluid substance 10 stored in internal cavity 121. Intake tube 126 may have a longitudinal length that extends between a first (top) end, coupled to outlet port 124, and a second (bottom) end 127 disposed within internal cavity 121. It should be appreciated that the longitudinal length of intake tube 126 may be such that second end 127 is positioned below a surface level of the fluid substance 10 stored in internal cavity 121. Stated differently, second end 127 may be submerged within fluid substance 10 such that intake tube 126 may be in fluid communication with fluid substance 10 via an opening at second end 127. In the embodiment, intake tube 126 may be sized to have a diameter that is equal to or greater than the diameter of outlet lines 134A, 134B.

Still referring to FIG. 3, a predetermined dose of fluid substance 10 stored in fluid container 120 may be at least partially based on a volume of fluid substance 10 within internal cavity 121. Particularly, the predetermined dose may be based on a distance between a surface elevation of fluid substance 10 in internal cavity 121 and a position of second end 127 relative to internal cavity 121. As described in detail below, fluid container 120 may be configured to divert fluid substance 10 from internal cavity 121 to outlet line 134 (via outlet port 124) in response to receiving a pressurized medium in internal cavity 121 from inlet line 132 (via inlet port 122). In this instance, an increased pressure within internal cavity 121 may cause at least a portion of fluid substance 10 to travel into intake tube 126 via second end 127, and toward outlet port 124 for receipt within outlet line 134.

In some embodiments, a diameter of internal cavity 121 may be at least partially determinative of an inlet pressure generated within fluid container 120. For example, decreasing the diameter of internal cavity 121 may generate increased pressure when the pressurized medium is received within fluid container 120. It should be understood that a force applied to the fluid substance 10 stored in fluid container 120 may be increased by reducing a cross-sectional dimension of internal cavity 121, thereby improving a deliverability of the fluid substance 10 from fluid container 120 to shaft 112.

Fluid container 120 may further include a rotatable joint 128 coupled between outlet port 124 and outlet line 134. Rotatable joint 128 may be configured to facilitate rotation of outlet line 134 relative to outlet port 124, such as, for example, in response to rotation of shaft 112 relative to body 102. Accordingly, fluid container 120 may be configured to maintain fluid communication between outlet line 134 and outlet port 124 during rotation of shaft 112 (and outlet line 134 disposed therein).

Referring now to FIG. 4, distal end 116 of shaft 112 is depicted with a distal opening of each of fluid line 132C, first outlet line 134A, and second outlet line 1346 positioned adjacent to opening 118 at distal end 116. It should be appreciated that the plurality of lines 132C, 134A, 134B may be arranged in various suitable orientations and/or positions relative to one another than that shown. As briefly described above, in lieu of fluid line 132C, first outlet line 134A, and second outlet line 134B extending through shaft 112, shaft 112 may include one or more channels coupled to each of the lines 132C, 134A, 134B. In this instance, the first fluid substance 10, a second fluid substance 10 in a different container than first fluid substance 10, and the pressurized medium may be directly received within a respective channel of shaft 112. Accordingly, the first fluid substance 10, the second fluid substance 10, and pressurized medium remain separated from one another within shaft 112.

In exemplary use of medical device 100, shaft 112 may be initially positioned adjacent to a target treatment site within a subject, such as, for example, through the working channel of a medical instrument (e.g., endoscope, gastroscope, etc.). As described briefly above, the target treatment site may include areas (e.g., tissue) within a subject (e.g., patient) that may be prone to injury or delayed leakage, such as due to perforations, sutures, and the like. Referring back to FIG. 1, with distal end 116 facing the target treatment site, and body 102 positioned external to the subject, medical device 100 may be actuated to initiate application of the two fluid substances 10 to the target treatment site by applying a proximal force onto actuator 108.

Referring now to FIG. 2, actuation of actuator 108 may provide for a controlled release of the pressurized medium stored in pressurized medium source 130 and into each of first inlet line 132A, second inlet line 132B, and fluid line 132C. Pressurized medium source 130 may be configured to transfer portions of the pressurized medium (e.g., compressed gas) into each of first fluid container 120A and second fluid container 120B at a delivery rate of about 0.10 PSI to 80 PSI, such as between 40 PSI and 60 PSI. Particularly, a first portion of the pressurized medium may be directed to first fluid container 120A via first inlet line 132A, a second portion of the pressurized medium may be directed to second fluid container 120B via second inlet line 132B, and a third portion of the pressurized medium may be directed toward shaft 112 via fluid line 132C.

The portions of pressurized medium traveling through inlet lines 132A, 132B may enter the respective fluid containers 120A, 120B via inlet ports 122A, 122B. In some embodiments, the portions of pressurized medium flowing through each of first inlet line 132A, second inlet line 132B, and fluid line 132C may vary relative to one another. For example, a pressurized release of the medium may be selectively adjusted based on a unique viscosity of the first fluid substance 10 and/or the second fluid substance 10 stored in each of the respective fluid containers 120A, 120B.

Referring now to FIG. 3, upon entry of the pressurized medium into fluid containers 120A, 120B, the pressurized medium may generate an increased pressure within the atmosphere of internal cavity 121, thereby pushing the first and second fluid substances 10 downward (e.g., away from inlet port 122) relative to internal cavity 121. At least a portion of the first and second fluid substances 10 may be diverted through the respective intake tubes 126 via the opening at second end 127. In this instance, portions of each of the fluid substances 10 may be urged through intake tubes 126 and toward the respective outlet ports 124 until the fluid substances 10 are directed outward from the fluid container 120A, 120B and into the corresponding outlet line 134A, 134B. As described in greater detail herein, medical device

100 may be configured such that the pressurized medium released from pressurized medium source 130 and delivered into fluid containers 120A, 120B may be at similar or varying pressures (e.g., pound-force per square inch), such that the first and second fluid substances 10 may be delivered to the corresponding outlet line 134A, 134B at similar or varying velocities relative to one another.

It should be appreciated that the first fluid substance 10 and the second fluid substance 10 may be delivered from the respective fluid containers 120A, 120B and into shaft 112 separately from one another, such that the fluid substances 10 do not interact or mix with one another at any point within medical device 100. Stated differently, the first fluid substance 10 is isolated from the second fluid substance 10 throughout a travel path defined by the fluidic system of medical device 100, such that a mixture of the fluid substances 10 may only occur externally from body 102, canister 110, and shaft 112.

In some embodiments, one or more of fluid containers 120A, 120B may include an inlet valve and/or outlet valve (or other suitable mechanism) for controlling a resulting delivery rate and/or volume of the fluid substance 10 sent to the corresponding outlet line 134A, 134B. In this instance, a user of medical device 100 may selectively control the delivery of one or more fluid substances 10 in response to actuating the valve(s). In other embodiments, an intracellular composition of the respective fluid substances 10 may at least partially determine a delivery rate and/or volume of the fluid substance 10 delivered to outline lines 134A, 134B despite each fluid container 120A, 120B receiving a similar pressure of medium from pressurized medium source 130.

Referring back to FIG. 4, the first fluid substance 10 may exit first outlet line 134A and the second fluid substance 10 may exit second outlet line 134B at distal end 116. The pressurized medium released from pressurized medium source 130 may also exit medical device 100 at distal end 116 via fluid line 132C. Due to the generally high viscosity of the first and second fluid substances 10, the fluid substances 10 may exit the respective outlet line 134A, 134B slowly in the form of a plurality of droplets. Each of the first fluid substance 10 and the second fluid substance 10 may encounter a stream of pressurized medium exiting distal end 116 (via fluid line 132C) simultaneously as the pair of fluid substances 10 exit distal end 116. It should be appreciated that the first and second fluid substances 10 may be ejected from distal end 116 at a first velocity, and the pressurized medium may be ejected from distal end 116 at a second velocity that is greater than the first velocity. In some embodiments, the first fluid substance 10 may have a different viscosity than the second fluid substance 10, such that the pair of fluid substances 10 may drop out of distal end 116 at different rates.

Medical device 100 may be configured to direct the pressurized medium into contact with the plurality of droplets of the first and second fluid substances 10. For example, gravitational forces may cause the droplets of the pair of fluid substance 10 to fall into alignment with the stream of pressurized medium released from fluid line 132C. In this instance, the pressurized medium may mix the first fluid substance 10 with the second fluid substance 10 at a location external of shaft 112 (e.g., at a position distal from distal end 116).

Further, the pressurized medium may be configured to exit distal end 116 at a predefined velocity capable of disassembling a polymer chain of the plurality of droplets of each of the first fluid substance 10 and the second fluid substance 10. Stated differently, the stream of medium from fluid line 132C may be released with a relatively high velocity such that the pressure applied to the plurality of droplets of first fluid substance 10 and second fluid substance 10 may cause the chemical bonds of said droplets to break apart. The predefined velocity may be at least partially determinative based on a release pressure of the medium from pressurized medium source 130, which may range from about 0 PSI to about 100 PSI, such as 0.1 PSI to about 80 PSI.

Accordingly, the pressurized medium may be configured to atomize the plurality of droplets of the first fluid substance 10 and the second fluid substance 10 at a position distal of shaft 112. In other words, the pressurized medium may create an atomization effect by mixing the first and second fluid substances 10 with one another, and spraying the resulting solution mixture onto the target treatment site. For example, the first and second fluid substances 10 may be mixed at a 1:1 ratio relative to one another. As described above, the first and second fluid substances 10 may be mixed at various other ratios based on various parameters, including but not limited to, a varying pressure of medium received in each fluid container 120A, 120B from pressurized medium source 130, selectively controlling an inlet valve or outlet valve, a varying intracellular composition of the respective fluid substances 10 stored in each fluid container 120A, 120B, etc.

In some embodiments, the pressurized medium released from pressurized medium source 130 may be configured to generate a targeted stream of the solution mixture sprayed outwardly from distal end 116. In this instance, medical device 100 may be configured to control a direction of delivery of the solution mixture from shaft 112, such as in an orientation opposing gravity. Alternatively, the pressurized medium may break the droplets of the first and second fluid substances 10 to generate a targeted mist of the solution mixture. Directional delivery of a stream and/or mist of the solution mixture may be further controlled in response to actuation (e.g., rotation) of nozzle 109, causing a corresponding rotation of shaft 112. It should be appreciated that the solution resulting from the mixture of the first and second fluid substances 10 may form an adhesive composition (e.g., glue) capable of providing a protective barrier at the target treatment site.

Each of the aforementioned systems, devices, assemblies, and methods may be used to deliver and mix multiple different substances during application to target tissue. By providing a medical device capable of delivering multiple substances in an isolated state from one another during application to the target tissue, instances of delivering inaccurate compound ratios of the individual substances may be minimized, thereby increasing an effectiveness in treating the target site. In this instance, a user may reduce overall procedure time, increase efficiency of procedures, and/or avoid unnecessary harm to a subject's body caused by subsequent procedures of delivering additional substances to the target site due to inaccurate, initial application quantities of the substances.

It will be apparent to those skilled in the art that various modifications and variations may be made in the disclosed devices and methods without departing from the scope of the disclosure. Other aspects of the disclosure will be apparent to those skilled in the art from consideration of the specification and practice of the features disclosed herein. It is intended that the specification and examples be considered as exemplary only.

We claim:

1. A medical device, comprising:
a body;
a first container storing a first substance;
a second container storing a second substance;
a canister coupled to a distal portion of the body, wherein the first container and the second container are disposed within the canister;
a shaft extending distally from the body and having a distal end; and
a pressure source in fluid communication with the first container, the second container, and the shaft, wherein pressurized medium from the pressure source is configured to:
  (i) deliver the first substance through the shaft and out of the distal end;
  (ii) deliver the second substance through the shaft, separate from the first substance, and out of the distal end; and
  (iii) be delivered through the shaft separate from the first substance and the second substance, and out of the distal end, such that the pressurized medium mixes the first substance and the second substance externally of the shaft as the first and second substances exit the distal end.

2. The medical device of claim 1, wherein the first substance and the second substance exit the distal end of the shaft in the form of a plurality of droplets.

3. The medical device of claim 2, wherein the pressurized medium is configured to exit the distal end of the shaft at a predefined velocity to disassemble a polymer chain of the plurality of droplets of each of the first substance and the second substance.

4. The medical device of claim 2, wherein the pressurized medium is configured to atomize the plurality of droplets of the first substance and the second substance at a position distal to the distal end of the shaft.

5. The medical device of claim 2, wherein the pressurized medium is configured to generate a stream sprayed from the distal end of the shaft.

6. The medical device of claim 2, wherein the pressurized medium is configured to generate a mist sprayed from the distal end of the shaft.

7. The medical device of claim 1, wherein the shaft includes a first channel for receiving the first substance, a second channel for receiving the second substance, and a third channel for receiving the pressurized medium.

8. The medical device of claim 7, wherein the first container is in fluid communication with the pressure source and the first channel of the shaft, and wherein the second container is in fluid communication with the pressure source and the second channel of the shaft.

9. The medical device of claim 7, wherein the first container includes a first intake tube extending into a cavity of the first container, wherein the first intake tube has an opening that is positioned below a surface level of the first substance within the cavity.

10. The medical device of claim 9, wherein the pressurized medium is configured to enter the first container and generate pressure within the cavity to transfer the first substance through the opening and up the first intake tube.

11. The medical device of claim 7, wherein the pressure source is configured to simultaneously deliver the pressurized medium to the first container, the second container, and the third channel of the shaft.

12. The medical device of claim 1, wherein the pressure source is disposed within the body and includes a gas canister, wherein the pressurized medium includes compressed gas stored in the gas canister in a supercritical or liquid form at about 850 psi.

13. The medical device of claim 1, wherein the first substance and the second substance each has a viscosity greater than 1 centipoise.

14. The medical device of claim 1, wherein the canister is removably coupled to the distal portion of the body.

15. The medical device of claim 14, wherein the body includes an actuator, wherein actuating the actuator decouples the canister from the body.

16. A medical device, comprising:
a body;
a first container storing a first substance;
a second container storing a second substance;
a nozzle rotatably coupled to the body;
a shaft extending distally from the nozzle and having a distal end, wherein the shaft is fixedly coupled to the nozzle; and
a pressure source in fluid communication with the first container, the second container, and the shaft, wherein pressurized medium from the pressure source is configured to:
  (i) deliver the first substance through the shaft and out of the distal end;
  (ii) deliver the second substance through the shaft, separate from the first substance, and out of the distal end; and
  (iii) be delivered through the shaft separate from the first substance and the second substance, and out of the distal end, such that the pressurized medium mixes the first substance and the second substance externally of the shaft as the first and second substances exit the distal end.

17. The medical device of claim 16, wherein the first container includes a first conduit, wherein the second container includes a second conduit, wherein the first conduit and the second conduit each extend through the nozzle and the shaft to the distal end of the shaft, and wherein the first conduit and the second conduit are configured to rotate with the shaft and nozzle relative to the body.

18. A medical device, comprising:
a body;
a shaft extending distally from the body and having a distal end, where in the shaft is rotatable relative to the body;
a plurality of containers, each of the plurality of containers is configured to store a substance, wherein each of the plurality of containers include:
  a rotatable joint rotatably coupled to the respective container, and
  a conduit fixedly coupled to the rotatable joint,
  wherein the conduit is configured to rotate with the rotatable joint; and
a pressure source in fluid communication with each of the plurality of containers and the shaft,
wherein rotation of the shaft relative to the body causes rotation of the conduit of each container of the plurality of containers relative to the body.

19. The medical device of claim 18, wherein pressurized medium from the pressure source is configured to:
  (i) deliver a first substance from one of the plurality of containers through the shaft and out of the distal end;
  (ii) deliver a second substance from another of the plurality of containers through the shaft, separate from the first substance, and out of the distal end; and (ii be delivered through the shaft separate from the first substance and the second substance, and out of the distal end, such that the pressurized medium mixes the first substance and the second substance externally of the shaft as the first and second substances exit the distal end.

20. The medical device of claim 18 further comprising:
a canister detachably coupled to the body, wherein each container of the plurality of containers is disposed within the canister.

* * * * *